United States Patent [19]

Hayakawa et al.

[11] Patent Number: 4,895,944
[45] Date of Patent: Jan. 23, 1990

[54] BENZOXAZINE INTERMEDIATES

[75] Inventors: Isao Hayakawa; Shohgo Atarashi, both of Tokyo, Japan

[73] Assignee: Daiichi Seiyaku Company, Ltd., Tokyo, Japan

[21] Appl. No.: 138,117

[22] Filed: Dec. 28, 1987

[30] Foreign Application Priority Data

Dec. 25, 1986 [JP] Japan .................. 61-314095

[51] Int. Cl.$^4$ .......................... C07D 265/36
[52] U.S. Cl. .................................. 544/105
[58] Field of Search ........................... 544/105

[56] References Cited

U.S. PATENT DOCUMENTS 4,382,892 5/1983 Hayakawa et al. ............ 544/101 X
4,601,745 7/1986 Moser ............................ 544/105 X

FOREIGN PATENT DOCUMENTS 0047005 3/1982 European Pat. Off. .
0206283 12/1986 European Pat. Off. .
1246171 1/1986 Japan .

OTHER PUBLICATIONS

Smith et al., Chemical Abstracts, vol. 95(1981) 132784e.
Chemical Abstracts, vol. 106, No. 3, Abstract No. 102 305c; p. 662, Mar. 30, 1987.
Chemical Abstracts, vol. 106, No. 13, Abstract No. 102 306d, p. 663, Mar. 30, 1987.
Chemical Abstracts, vol. 99, No. 11, Abstract No. 88, 227g, p. 574, Sep. 12, 1983.

Primary Examiner—Richard L. Raymond
Attorney, Agent, or Firm—Sughrue, Mion, Zinn, Macpeak & Seas

[57] ABSTRACT

An optically active 3,4-dihydrobenzoxazine derivative, a process for preparing the same and an intermediate of 2H-benzoxazine useful for synthesizing the above mentioned optically active 3,4-dihydrobenzoxazine are disclosed.

3 Claims, No Drawings

BENZOXAZINE INTERMEDIATES

FIELD OF THE INVENTION

This invention relates to optically active 3,4-dihydrobenzoxazine derivatives and to a process for preparing the same useful as intermediates for preparing excellent antibacterial agents.

BACKGROUND OF THE INVENTION

Ofloxacin (I), ((±)-9-fluoro-3-methyl-10-(4-methyl-1-piperazinyl)-7-oxo-2,3-dihydro-7H-pyrido[1,2,3-de][1,4]benzoxazine-6-carboxylic acid) is known and employed as an excellent synthetic antibacterial agent.

Ofloxacin has an asymmetric carbon atom at the 3-position and is obtained as a racemic mixture. Of the two isomers, the 3S-methyl compound (IS) which is represented by the following formula was confirmed to have higher activity and reduced toxicity in comparison with the racemic compound or 3R-methyl compound (IR).

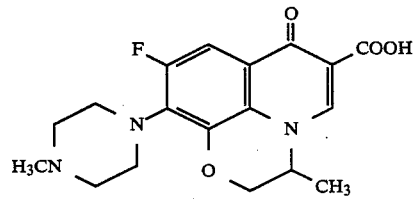
(I)

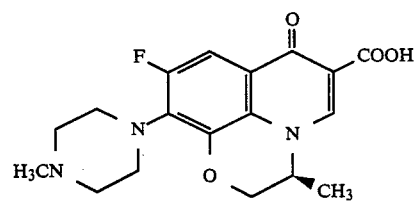
(IS)

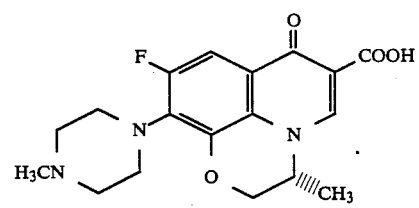
(IR)

The synthesis of compound represented by the formula (IS) was achieved by converting the optically active benzoxazine intermediates which were obtained by the optical resolution of appropriate racemic benzoxazine derivatives, as described in EP-A No. 206,283.

SUMMARY OF THE INVENTION

An object of this invention is to provide optically active isomers of 3-alkyl-3,4-dihydro-2H-[1,4]benzoxazine derivatives represented by the formula (III)

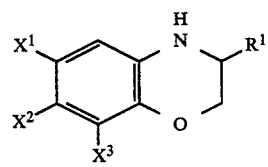
(III)

wherein $X^1$, $X^2$ and $X^3$, which may be the same or different, each represents a hydrogen atom or a halogen atom, and $R^1$ represents an alkyl group having 1 to 6 carbon atoms, and the salts thereof.

Another object of this invention is to provide novel intermediates represented by formula (II) below which are useful for synthesizing optically active 3-alkyl-3,4-dihydro-2H-[1,4]benzoxazine derivatives with chiral reducing agents.

A further object of this invention is to provide a process for preparing optically active isomers of 3,4-dihydro-2H-[1,4]benzoxazine derivatives (III) shown above by asymmetric reduction of 2H-[1,4]benzoxazine derivatives (II) shown below with chiral reducing agents.

After extensive investigations, it has been found that asymmetric reduction of 3-alkyl-2H-[1,4]benzoxazine by chiral reducing agents gave optically active 3-alkyl-3,4-dihydro-2H-[1,4]benzoxazine in high optical purity.

As a result of extensive investigations in synthesizing optically active 3-alkyl-3,4-dihydro-2H-[1,4]benzoxazine derivatives, especially the 3S-isomer, it has now been found that compounds having the formula (II) are useful as intermediates for synthesizing the optically active isomer of 3,4-dihydrobenzoxazines represented by the formula (IIIS) by reduction with chiral reducing agents as shown in the following reaction scheme:

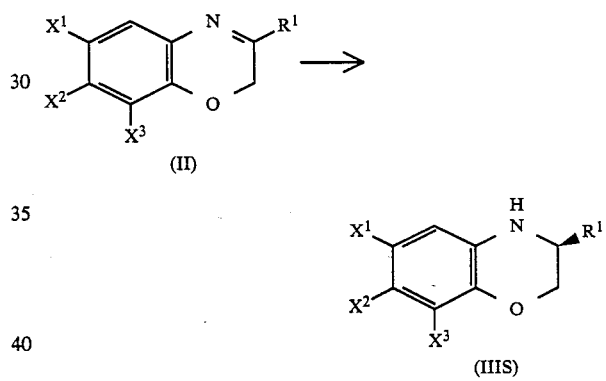

wherein $X^1$, $X^2$ and $X^3$, which may be the same or different, each represents a hydrogen atom or a halogen atom, such as a fluorine atom, a chlorine atom, and preferably $X^1$ is hydrogen and both $X^2$ and $X^3$ are fluorine atom; and $R^1$ represents an alkyl group having from 1 to 6 carbon atoms, such as a methyl group, an ethyl group, a propyl group and the like, and preferably a methyl group.

DETAILED DESCRIPTION OF THE INVENTION

As mentioned above, the 3S-isomer of Ofloxacin and its analogs are preferable. The synthesis of compound (IS) and its analogues is best achieved by starting from the optically active compound (IIIS). This optically active compound (IIIS) is easily prepared by asymmetric reduction of compound (II) using chiral reducing agents. Suitable chiral reducing agents include a number of different reagents applicable for the present invention, e.g., chiral complex of borohydrides or aluminum hydrides, and chiral complex of metal catalysts. Such complexes are exemplified as follows: chiral acyloxy borohydrides (as disclosed in T. Iwakuma et al., Chem. Pharm. Bull., 31, 70 (1983)); complex of chiral amino alcohol and borane (as disclosed in S. Ituno et al., J. Chem. Sco., Perkin Trans. I, 2039 (1985)); potassium 9-0-(1,2:5,6-di-O-isopropylidene-alpha-D-glucofuranosyl)-9-boratabicyclo[3,3,1]nonane (as disclosed in H. C. Brown, *J. Org. Chem.*, 51, 3396 (1986); complex of (−)-ephedrin, N-ethylaniline and lithium aluminum hydride (as disclosed in K. Koga et al., *Tetra. Lett.*, 275 (1980)); complex of (S)-2-(2,6-xylidomethyl)-pyrrolidine and lithium aluminum hydride (as disclosed in M. Mukaiyama et al., *Heterocycles*, 12, 499 (1979); complex of 2,2′-dihydroxy1,1′-binaphthyl, hydroxylic compound and lithium aluminum hydride (as disclosed in R. Noyori et al., *J. Am. Chem. Soc.*, 101, 3129 (1979)); nickel-palladium-kieselguhr modified with tartaric acid (as disclosed in Y. Orido et al., *J. Synth. Org. Chem., Japan*, 34, 672 (1976)); complex of pyrrolidinobiphosphines and rhodium (as disclosed in K. Achiwa et al., *Tetra. Lett.*, 4477 (1986)) and the like. The disclosures of these references are herein incorporated by reference. Among these chiral reducing agents, chiral alkali metal acyloxy borohydrides are most preferable, for high optical purity of the product is attained with this reagent. Further, this reagent is easily prepared from sodium borohydride and proline derivatives and the reagent is less dangerous than the aluminum complex.

The reagent is represented by the following formula:

$$MBH_{4-n}(RCOO)_n$$

wherein M represents an alkali metal such as lithium, sodium and potassium; and n represents an integer of from 1 to 3; and RCOO represents an acyloxy residue such as an acetoxy, a propionyloxy, a chloroacetoxy, or a benzoyloxy residue or a residue represented by the following formula:

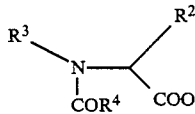

wherein $R^2$ and $R^3$, which may be the same or different, each represents a hydrogen atom or an alkyl group having 1 to 6 carbon atoms such as a methyl group, an ethyl group, an isopropyl group, or an aralkyl group, for example, an unsubstituted or substituted phenylalkyl group having from 1 to 3 carbon atoms in the alkyl moiety thereof, such as a benzyl group, or substituted benzyl group; or $R^2$ and $R^3$ may combine and represent a methylene chain such as $-(CH_2)_m-$, where m represents an integer of from 2 to 4; $R^4$ represents an alkyl group having from 1 to 6 carbon atoms such as a methyl group, an ethyl group, etc.; a phenyl group which may be substituted with alkyl group(s) having from 1 to 6 carbon atoms, halogen atom(s), nitro group(s), alkoxy group(s) having from 1 to 6 carbon atoms and the like; an alkoxy group having from 1 to 6 carbon atoms such as a methoxy group, an ethoxy group, an iso- or tert-butoxy group, etc.; or a phenylalkyloxy group in which the alkyl moiety has from 1 to 2 carbon atoms and the phenyl group may be substituted with alkyl group(s) having from 1 to 6 carbon atoms, halogen atom(s), nitro group(s), alkoxy group(s) having from 1 to 6 carbon atoms and the like.

As for the acyl residue of the chiral acyloxy borohydride, (S)-amino acid, especially N-acyl-(S)-proline, is most favourable; e.g., (S)-N-isobutyloxycarbonylproline or (S)-N-benzyloxycarbonylproline and the like. These chiral acyloxy borohydrides are easily prepared from alkali metal borohydride and N-acyl-(S)-proline in tetrahydrofuran as reported by Iwakuma et al. (*J. Synth. Org. Chem., Japan*, 41, 453 (1983); *Chem. Pharm. Bull.*, 31, 70 (1983)). The n which means a number of the acyloxy residue in the reducing agent is in the range of 1 to 3, and is preferably 3 for the higher optical purity of the reduced product as reported in literature references. The molar ratio of 2H-benzoxazine derivative (II) and the reducing agent is in the range of from 1:1 to 1:5, preferably 1:2.5.

The reduction with the chiral acyloxy borohydrides may be carried out in a solvent inert to the reaction, such as diethyl ether, 1,2-dimethoxyethane, acetonitrile, toluene, ethyl acetate, 1,1,2,2-tetrachloroethane, 1,1,2,2-tetrachloroethylene, 1,1-dichloroethane, 1,2-dichloroethane, dichloromethane and the like. Of these solvents, halogen-containing solvents are preferred. The amount of the solvent can be in the range of from 5 to 50 parts by volume, and preferably in the range of from 5 to 20 parts by volume, to the amount of the benzoxazine derivative (II). The reduction can be performed by mixing a solution of an acyloxy borohydride and a solution of 2H-benzoxazine in a solvent mentioned above. The chirality of the resulting reduction product corresponds to that of the ligand of the reducing agent used. That is, when acyloxy borohydride derived from S-amino acid is used, the reduction product has S-configuration.

Even when the optical purity of the product is not very high, optically pure 3,4-dihydrobenzoxazine is readily obtained from a crude mixture by a simple purification, e.g., recrystallization. The purification of a mixture in which one isomer is present in a larger amount than the other is much easier than a mixture containing an equal amount of the isomers.

The reduction can be performed at a temperature in the range of from about −60° C. to about 60° C., preferably from −45° C. to 20° C., for a period of from about 10 minutes to about 48 hours.

The end of the reaction can be detected by TLC.

This invention is illustrated in greater detail by reference to the following examples, but it should be understood that they are not intended to limit the present invention. Unless otherwise indicated herein, all parts, percents, ratios and the like are by weight.

REFERENCE EXAMPLE 1

2-(2,2-Ethylenedioxypropyloxy)-3,4-difluoronitrobenzene (2)

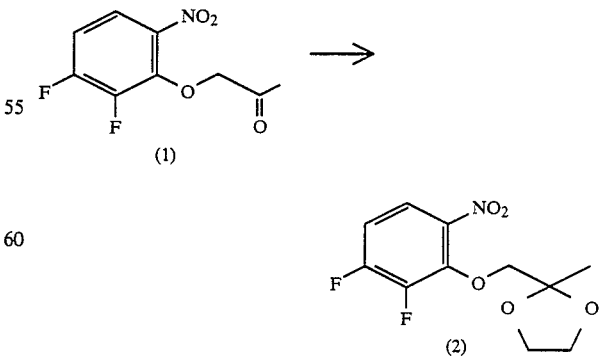

A mixture of 4.6 g of 3,4-difluoro-2-(2-oxopropyloxy)nitrobenzene (1), 1,5 g of ethylene glycol, a catalytic amount of p-toluenesulfonic acid and 60 ml of anhydrous benzene was heated under reflux for 18 hours while removing water using a Dean-Stark apparatus. After cooling, the mixture was washed twice with a saturated sodium bicarbonate aqueous solution and with water. The solvent was removed in vacuo, and the residue was purified through an 80 g silicagel column which was eluted by chloroform to yield 5 g of a nitro derivative as a yellow oily product (2).

$^1$H-NMR(CDCl$_3$) δ ppm: 1.50 (3H, s, —CH$_3$), 4.00 (4H, s, —OCH$_2$CH$_2$O—), 4.16 (2H, AB-q, J=10.5 Hz, —CH$_2$C<), 7.0 (1H, ddd, J=10.5, 9, 8 Hz, arm.), 7.66 (1H, ddd, J=9.5, 5.5, 3 Hz, arm.)

REFERENCE EXAMPLE 2

2-(2,2-Ethylenedioxypropyloxy)-3,4-difluoroaniline (3)

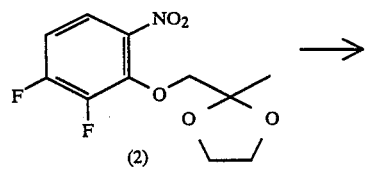

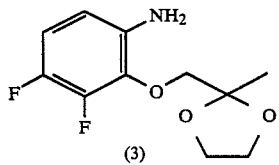

To a solution of 1.6 g of the nitro derivative (2) obtained as described in Reference Example 1 in 70 ml of anhydrous ethanol was added 2.0 g of 5%-palladium on charcoal (50% wet). The mixture was shaken under a hydrogen atmosphere until hydrogen absorption ceased. After removing the catalyst by filtration, the solvent of the filtrate was removed under reduced pressure to give 1.3 g of an aniline as an oily product (3).

$^1$H-NMR(CDCl$_3$) δ ppm: 1.50 (3H, s, —CH3), 3.96 (2H, s, —OCH$_2$C<), 4.04 (4H, s, —OCH$_2$CH$_2$O), 3.8–4.2 (2H, br.m, NH$_2$), 6.36 (1H, ddd, J=9.5, 5.5, 3 Hz, arm.), 6.70 (1H, ddd, J=11, 9.5, 3 Hz, arm.)

REFERENCE EXAMPLE 3

7,8-Difluoro-3-methyl-2H-[1,4]benzoxazine (II)

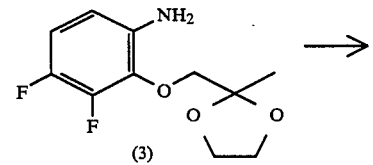

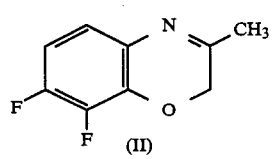

A mixture of 1.3 g of the aniline (3) obtained as described in Reference Example 2, 30 ml of 2N hydrochloric acid and 30 ml of benzene was heated under reflux for 2 hours. After cooling, sodium bicarbonate was added until the aqueous layer was neutralized. The mixture was extracted with benzene three times, and the extract was washed with water, then dried. The solvent was removed under reduced pressure to yield a benzoxazine (II) as a yellow oily product.

$^1$H-NMR(CDCl$_3$) δ ppm: 2.16 (3H, s, —CH$_3$), 4.60 (2H, s, —OCH$_2$—), 6.26 (1H, ddd, J=9, 5, 3 Hz, C$_5$H), 6.5–6.8 (1H, m, C$_6$-H)

EXAMPLE 1

(S)-7,8-difluoro-3,4-dihydro-3-methyl-2H-[1,4]benzoxazine (IIIS)

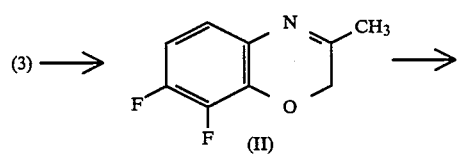

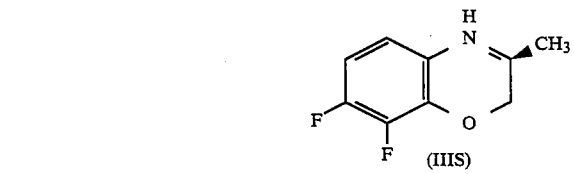

A mixture of 1.81 g of the aniline (3) and 9 ml of 35% hydrochloric acid was stirred at 70° to 80° C. for 1 minute. The mixture was cooled on an ice bath and this solution was added dropwise to a 14.5 ml of ice-cooled 28% aqueous ammonia. Precipitated imine (II) was extracted with three 10 ml portions of dichloromethane, and the extract was washed with 5 ml of saturated sodium chloride aqueous solution and dried over anhydrous magnesium sulfate. The solvent was removed under reduced pressure to yield a crystalline residue. The NMR spectrum of this residue was identical to that obtained in Reference Example 2 and this melted at 51.2° C.

Mass spectrum: m/Z=183 (M+)

Elementary Analysis for C$_9$H$_7$F$_2$NO:

| | | | | | |
|---|---|---|---|---|---|
| Calculated: | C | 59.02; | H | 3.85; | N 7.65 |
| Found: | C | 58.91; | H | 3.89; | N 7.49 |

Tris[(S)-N-isobutyloxycarbonylproplyloxy]hydroborate was prepared from sodium borohydride and N-isobutyloxycarbonyl-(S)-proline and a solution of 15.5 g of this hydride in 30 ml of anhydrous dichloromethane was cooled to −41° C. To this was added a solution of the imine (II) obtained above in 15 ml of anhydrous dichloromethane was added under a nitrogen atmosphere (at the end of the addition, the internal temperature raised to −34° C.). The reaction mixture was stirred at −40° to −5° C. for 40 minutes, then the mixture was washed with a 5% citric acid aqueous solution, 10% sodium carbonate aqueous solution and water. The amount of (S)-7,8-difluoro-3,4-dihydro-3-methyl-2H-[1,4]benzoxazine (IIIS) was calculated to be 1.2945 g by the quantitative analysis of the dichloromethane solution using high pressure liquid chromatography (column: YMC-Pack®, A-312 ODS; eluent: mixture of acetonitrile and water (5:3 by volume); speed: 1 ml/min.). The ratio of the S-isomer and R-isomer was 21:3:1 (91% ee*) using the analytical method mentioned in Example 2 below.

* Note: "% ee" is an abbreviation for %. enantiomer excess, and is a measure of an optical purity of an optically active compound (see, for example, *Asymmetric Synthesis*, Vol. 1, p. 45, 60, Academic Press, New York (1983), edited by J. D. Morrison et al.). The % ee is calculated as follows.

$$\frac{[R] - [S]}{[R] + [S]} \times 100$$

wherein [R] represents a molar ratio of one isomer in percent, and [S] represents that of the other isomer, when [R]+[S] is taken as 100%.

EXAMPLE 2

(S)-7,8-difluoro-3,4-dihydro-3-methyl-2H-[1,4]benzoxazine (IIIS)

To a mixture of 3.7 g of tris[(S)-N-benzyloxycarbonylpropyloxy]hydroborate prepared conventionally from sodium borohydride and (S)-N-benzyloxyproline and 30 ml of anhydrous dichloromethane was added a solution of 250 mg of the cyclic imine (II) in 15 ml of anhydrous dichloromethane and the resulting mixture was stirred at room temperature (about 20° to 30° C.) for 24 hours. The mixture was washed with a saturated sodium bicarbonate aqueous solution and water, then dried over anhydrous sodium sulfate. The solvent was removed in vacuo, and the residue was purified through a 40 g silica-gel column eluted with chloroform to yield 150 mg of yellowish oily (S)-7,8-difluoro-3,4-dihydro-3-methyl-2H-[1,4]benzoxazine (IIIS). The Rf value on TLC and the NMR spectrum were identical to those of the racemic compound. The optical purity of this product was determined in the form of the N-3,5-dinitrobenzoyl derivative which was obtained by heating a mixture of 3,5-dinitrobenzoyl chloride (54 mg), the product (III) (19.7 mg), pyridine (16.4 mg) and tetrahydrofuran (0.5 ml) at 30° to 40° C. for 30 minutes. The analysis was performed by high pressure liquid chromatography (column: OA-4200, 4.6 mm x 250 mm, available from Sumitomo Chemical Co., Ltd.; solvent: n-hexane:1,2-dichloroethane:ethanol =10:0.9:0.1 by volume; speed: 1.0 ml/min.). It was revealed that the more preferable S-isomer (IIIS) was obtained as a major product in a ratio of 89:11 (78% ee) by this reduction.

REFERENCE EXAMPLE 4

To a solution of 150 mg of the benzoxazine derivative obtained as described in Example 2 and 0.2 ml of pyridine in 5 ml of anhydrous dichloromethane was added dropwise a dichloromethane (5 ml) solution of the acid chloride prepared from 300 mg of (S)-N-p-toluenesulfonylproline and thionyl chloride, and the mixture was stirred at room temperature for 4 hours. The reaction mixture was washed with 10% hydrochloric acid and a saturated sodium bicarbonate aqueous solution, and then dried over anhydrous sodium sulfate. The solvent was removed under reduced pressure, and the oily residue was purified through a silica-gel column eluted with a mixture of benzene and ethyl acetate (3:1 by volume) to yield an oily product. This product was obtained as crystals after the oil was dissolved in 2.5 ml of ethanol and the solution was allowed stand at room temperature for a day. Ethanol was removed under reduced pressure. To the crystalline residue was added a mixture of diethyl ether and n-hexane, then a crystalline product was collected by filtration. Drying under reduced pressure, 270 mg of 3S-(+)-7,8-difluoro-3,4-dihydro-3-methyl-4-[(S)-N-Ptoluenesulfonyl]prolyl-2H-[1,4]benzoxazine was obtained ; m.p.: 107°-108° C.

A solution of 250 mg of the product obtained as described above and 5 ml of a 1N sodium hydroxide aqueous solution and 10 ml of ethanol was heated under reflux for 3 hours. The solvent was removed under reduced pressure and the oily residue was extracted with benzene. The extract was washed with a saturated sodium chloride aqueous solution and dried over anhydrous sodium sulfate. After removing the solvent under reduced pressure, the residue was purified through a 200 g of silica-gel column eluted with benzene to yield 100 mg of oily (S)-(-)-7,8-difluoro-3,4-dihydro-3-methyl-2H-[1,4]benzoxazine (IIIS); $[\alpha]_D - 9.4°$ (c=1.50, chloroform).

REFERENCE EXAMPLE 5

A mixture of 100 mg of (S)-(-)-7,8-difluoro-3,4-dihydro-3-methyl-2H-[1,4]benzoxazine (IIIS) and 160 mg of diethyl ethoxymethylenemalonate was heated at 130° to 140° C. in vacuo for 1 hour. After cooling, the reaction mixture was dissolved in 1 ml of acetic anhydride. This solution was cooled on an ice bath and to this was added 1.6 ml of a mixture of acetic anhydride and concentrated sulfuric acid (2:1 by volume) dropwise. The mixture was stirred at room temperature for 1 hour, then heated at 50° to 60° C. for 30 minutes. To the mixture was added ice and water, the mixture was neutralized by adding powdered potassium carbonate. After the reaction mixture was extracted with chloroform, the extract was washed with a saturated sodium bicarbonate aqueous solution and a saturated sodium chloride aqueous solution and dried over anhydrous sodium sulfate. The solvent was removed under reduced pressure and diethyl ether was added to the residue. The crystalline product was collected by filtration to yield 125 mg of ethyl (S)-(-)-7,8-difluoro-2,3-dihydro-3-methyl-7-oxo-7H-pyrido[1,2,3-de][1,4] benzoxazine-6-carboxylate; m.p.: 257°-258° C.; $[\alpha]_D - 68.1°$ (c=0.25, acetic acid).

A solution of 120 mg of the ester derivative obtained above, 3 ml of concentrated hydrochloric acid and 2 ml of acetic acid was heated under reflux for 3 hours. After cooling, the resulting crystalline product was collected by filtration and washed successively with water, ethanol and diethyl ether, and dried to yield 100 mg of (S)-(—)-7,8-difluoro-2,3-dihydro-3-methyl-7-oxo-7H-pyrido-[1,2,3-de][1,4]benzoxazine-6-carboxylic acid; m.p.>300° C.; $[\alpha]_D - 65.6°$(c=0.985, DMSO).

A mixture of 100 mg of the acid derivative obtained as described above, 1 ml of boron trifluoride diethyl etherate and 5 ml of diethyl ether was stirred at room temperature for 5 hours. The solvent was removed by decantation and diethyl ether was added to the residue. The solid mass was collected by filtration and washed with diethyl ether and dried under reduced pressure. This solid was dissolved in 2 ml of dimethyl sulfoxide and to this were added 0.2 ml of triethylamine and 0.5 ml of N-methylpiperazine. The mixture was stirred at room temperature for 18 hours. The solvent was removed under reduced pressure and diethyl ether was added to the residue. The collected yellow powder was suspended in 5 ml of 95% methanol and to this was added 1 ml of triethylamine. The mixture was heated under reflux for 25 hours. The solvent was removed under reduced pressure and the residue was dissolved in 10 ml of 10% hydrochloric acid. After this solution was extracted with chloroform three times, the aqueous layer was rendered basic to pH 11 using a sodium hydroxide aqueous solution. The pH of this solution was readjusted to 7.3 using 1N hydrochloric acid, and the solution was extracted with three 15 ml portions of chloroform. After drying over anhydrous sodium sulfate, the solvent was removed under reduced pressure The crystalline residue was recrystallized from a mixture of ethanol and diethyl ether to yield 83 mg of (S)-(-)-9-fluoro-2,3-dihydro-3-methyl-10-(4-methyl-1-piperazinyl)-7-oxo-7H-pyrido-[1,2,3-de][1,4]benzoxazine-6-carboxylic acid (IS); m.p.: 226°–230° C. (dec.); $[\alpha]_D$ —76.90° (c=0.655, 0.05N-NaOH aqueous solution).

While the invention has been described in detail and with reference to specific embodiments thereof, it will be apparent to one skilled in the art that various changes and modifications can be made therein without departing from the spirit and scope thereof.

What is claimed is:

1. A 2H-benzoxazine compound represented by the formula (II)

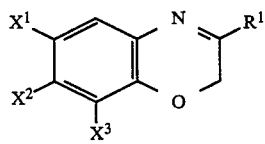

wherein $X^1$ represents a hydrogen atom or a halogen atom, $X^2$ and $X^3$ each represents a halogen atom, and $R^1$ represents an alkyl group having 1 to 6 carbon atoms, and the salts thereof.

2. A benzoxazine compound of 7,8-difluoro-3-methyl-2H-benzoxazine according to claim 1.

3. A compound of claim 1, wherein $X^1$ is a hydrogen atom.

* * * * *